US012758589B2

(12) United States Patent
Hebert et al.

(10) Patent No.: US 12,758,589 B2
(45) Date of Patent: Oct. 13, 2026

(54) COMPOSITIONS AND METHODS FOR USING TRANSPLANTED MICROGLIA AS A VEHICLE FOR WIDESPREAD DELIVERY OF CELLS AND OTHER BIOLOGIC AGENTS TO THE BRAIN

(71) Applicant: Albert Einstein College of Medicine, Bronx, NY (US)

(72) Inventors: Jean M. Hebert, Bronx, NY (US); Marta Gronska-Peski, Bronx, NY (US); Hiroko Nobuta, New Brunswick, NJ (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 908 days.

(21) Appl. No.: 17/922,098

(22) PCT Filed: Apr. 8, 2021

(86) PCT No.: PCT/US2021/026419
§ 371 (c)(1),
(2) Date: Oct. 28, 2022

(87) PCT Pub. No.: WO2021/221879
PCT Pub. Date: Nov. 4, 2021

(65) Prior Publication Data

US 2023/0165906 A1 Jun. 1, 2023

Related U.S. Application Data

(60) Provisional application No. 63/018,798, filed on May 1, 2020.

(51) Int. Cl.
*A61K 35/30* (2015.01)
*A61K 31/444* (2006.01)
*C07K 14/715* (2006.01)

(52) U.S. Cl.
CPC ............ *A61K 35/30* (2013.01); *A61K 31/444* (2013.01); *C07K 14/7153* (2013.01)

(58) Field of Classification Search
None
See application file for complete search history.

(56) References Cited

U.S. PATENT DOCUMENTS

2015/0167008 A1 6/2015 Bennett et al.
2020/0038439 A1 2/2020 Biffi et al.
2023/0081264 A1* 3/2023 Bennett .................... C12N 9/12 424/93.7

FOREIGN PATENT DOCUMENTS

NO 2017210684 A1 12/2017
WO 2018136434 A1 7/2018
WO 2019118951 A1 6/2019

OTHER PUBLICATIONS

Capotondo et al. "Brain conditioning is instrumental for successful microglia reconstitution following hematopoietic stem cell transplantation." Proceedings of the National Academy of Sciences 109.37 (2012): 15018-15023. (Year: 2012).*

Extended European Search Report for European Application 21796505.2, file Nov. 30, 2022; Search Report Date: May 2, 2024; 12 pages.

Han, J. et al.; "Enforced microglial depletion and repopulation as a promising strategy for the treatment of neurological disorders"; Glia, vol. 67, Issue No. 2; pp. 217-231 (2018) DOI:10.1002/GLIA.23529.

Paschalis, E. et al.; "Permanent neurological remodeling of the retina following infiltration of CSF1R inhibition-resistant peripheral monocytes"; PNAS, vol. 115, Issue No. 48; pp. E11359-E11361 (2018) DOI:10.1073/pnas.1807123115.

Sosna, J. et al.; "Early long-term administration of the CSF1R inhibitor PLX3397 ablates microglia and reduces accumulation of intraneuronal amyloid, neuritic plaque distribution and pre-fibrillar oligomers in 5XFAD mouse model of Alzheimer's diseases"; Molecular Neurodegeneration 13 (1) pp. 1-11 (2018) DOI:10.1186/s13024-018-0244-x.

Ballout, N. et al.; "Development and Maturation of Embryonic Cortical Neurons Grafted into the Damaged Adult Motor Cortex"; Frontiers in Neural Circuits, vol. 10, Article No. 55; 2016; 12 pages; doi: https://doi.org/10.3389/fncir.2016.00055.

Bruttger, J. et al.; "Genetic Cell Ablation Reveals Clusters of Local Self-Renewing Microglia in the Mammalian Central Nervous System"; Immunity, vol. 43; 2015; pp. 92-106.

Chase, A. et al.; "Imatinib sensitivity as a consequence of a CSF1R-Y571D mutation and CSF1/CSF1R signaling abnormalities in the cell line GDM1"; Leukemia, vol. 23; 2009; pp. 358-364.

Dagher, N. et al.; "Colony-stimulating factor 1 receptor inhibition prevents microglial plaque association and improves cognition in 3xTg-AD mice"; Journal of Neuroinflammation, vol. 12, Article No. 139; 2015; 14 pages DOI: 10.1186/s12974-015-0366-9.

Danielyan, L. et al.; "Intranasal delivery of bone marrow-derived mesenchymal stem cells, macrophages, and microglia to the brain in mouse models of Alzheimer's and Parkinson's disease"; Cell Transplantation, vol. 23, Supplement 1; 2014; pp. S123-S139.

Elmore, et al.; "Characterizing newly repopulated microglia in the adult mouse: impacts on animal behavior, cell morphology, and neuroinflammation"; PLoS One, vol. 10, e0122912; 2015; 18 pages; DOI: https://doi.org/10.1371/journal.pone.0122912.

(Continued)

*Primary Examiner* — Emily A Cordas
(74) *Attorney, Agent, or Firm* — CANTOR COLBURN LLP

(57) ABSTRACT

A method of replacing endogenous microglia of a subject's brain, e.g., an adult subject, with transplanted donor microglia includes depleting at least a portion of the endogenous microglia by administering to the subject a Colony Stimulating Factor 1 Receptor (CSFR1) inhibitor, wherein the CSFR1 inhibitor is blood-brain barrier permeable and pharmacologically ablates endogenous microglia; optionally stopping administration of the CSFR1 inhibitor for a time sufficient to prevent ablation of the transplanted donor microglia; and transplanting the donor microglia into the brain of the subject to provide the transplanted donor microglia.

2 Claims, 5 Drawing Sheets

(56) References Cited

OTHER PUBLICATIONS

Elmore, M. R. et al.; "Colony-stimulating factor 1 receptor signaling is necessary for microglia viability, unmasking a microglia progenitor cell in the adult brain"; Neuron, vol. 82, Issue No. 2; 2014; pp. 380-397.
Fricker-Gates, R.A. et al.; "Late stage immature neocortical neurons reconstruct interhemispheric connection and form synaptic contacts with increased efficiency in adult mouse cortex undergoing targeted neurodegeneration"; Journal of Neuroscience, vol. 22; 2002; pp. 4045-4056.
Gaillard, A. et al.; "Reestablishment of damaged adult motor pathways by grafted embryonic cortical neurons"; Nature Neuroscience, vol. 10, Issue No. 10; 2007; pp. 1294-1299.
Hébert, J. M. et al.; "Cell replacement to reverse brain aging: challenges, pitfalls, and opportunities"; Trends in Neuroscience, vol. 41, Issue No. 5; 2018; pp. 267-279.
Huang, Y. et al.; "Repopulated microglia are solely derived from the proliferation of residual microglia after acute depletion"; Nature Neuroscience, vol. 21; 2018; pp. 530-540.
International Search Report and Written Opinion for International Application PCT/US2021/026419; International Filing Date: Apr. 8, 2021; Date of Mailing: Jul. 29, 2021; 10 pages.
Michelsen, K. A. et al.; "Area-specific reestablishment of damaged circuits in the adult cerebral cortex by cortical neurons derived from mouse embryonic stem cells"; Neuron, vol. 85; 2015; pp. 982-997.
Muffat, et al.; "Efficient derivation of microglia-like cells from human pluripotent stem cells"; Nature Medicine, vol. 22, Issue No. 11; 2016; pp. 1358-1367.
Peron, S. et al.; "A delay between motor cortex lesions and neuronal transplantation enhances graft integration and improves repair and recovery"; Journal of Neuroscience, vol. 37, Issue No. 7; 2017; pp. 1820-1834.
Ponomarev, E. et al.; "MicroRNA-124 promotes microglia quiescence and suppresses EAE by deactivating macrophages via the C/EBP-α-PU.1 pathway"; Nature Medicine, vol. 17; 2011; pp. 64-70.
Shin, J. J., et al.; "Transplanted neuroblasts differentiate appropriately into projection neurons with correct neurotransmitter and receptor phenotype in neocortex undergoing targeted projection neuron degeneration"; The Journal of Neuroscience, vol. 20, Issue No. 19; 2000; pp. 7404-7416.
Spangeberg, E. et al.; "Sustained microglial depletion with CSF1R inhibitor impairs parenchymal plaque development in an Alzheimer's disease model"; Nature Communications, vol. 10, Issue No. 1, Article 3758; 2019; 21 pages.
Steinbeck, J. A. et al.; "Human embryonic stem cell-derived neurons establish region-specific, long-range projections in the adult brain"; Cell Mol. Life Science, vol. 69, Issue No. 3; 2012; pp. 461-470.
Wang, L. et al.; "CRISPR/Cas9-mediated targeted gene correction in amyotrophic lateral sclerosis patient iPSCs"; Protein Cell, vol. 8, Issue No. 5; 2017; pp. 365-378.

* cited by examiner

COMPOSITIONS AND METHODS FOR USING TRANSPLANTED MICROGLIA AS A VEHICLE FOR WIDESPREAD DELIVERY OF CELLS AND OTHER BIOLOGIC AGENTS TO THE BRAIN

CROSS REFERENCE TO RELATED APPLICATIONS

This application is a National Stage application of PCT/US2021/026419, filed Apr. 8, 2021, which claims priority to U.S. Provisional Application No. 63/018,798, filed May 1, 2020, which are incorporated by reference in their entirety herein.

FIELD OF THE DISCLOSURE

The present disclosure is related to compositions and methods for the transplantation and dispersion of microglia in the adult brain, for example to deliver therapeutic agents to broad areas of the brain to treat neurodegenerative and other diseases.

BACKGROUND

Microglia are a resident cell type of the brain, constituting 10-15% of all brain cells. Microglia have the ability to proliferate, migrate, and repopulate the brain when endogenous microglia are experimentally depleted. Microglia transplanted into the brain can be used for biologic drug delivery, or as cells for the treatment of neuropsychiatric and neurodegenerative disorders.

There is currently no efficient means of delivering biologics or cells to broad areas of the brain. Methods under development focus either on disrupting the blood-brain barrier or hijacking blood-brain barrier transporters, which are both hindered by inefficiency and deleterious side effects. Current drug delivery and cell transplantation methods into the brain are limited to focal delivery (near the site of injection). In addition, previous methods of transplanting and dispersing microglia are typically limited to transplantation around the time of birth. What is needed are compositions and methods for the transplantation of microglia to the adult brain.

BRIEF SUMMARY

In an aspect, a method of replacing endogenous microglia of a subject's brain, e.g., an adult subject, with transplanted donor microglia comprises depleting at least a portion of the endogenous microglia by administering to the subject a Colony Stimulating Factor 1 Receptor (CSF1R) inhibitor, wherein the CSF1R inhibitor is blood-brain barrier permeable and pharmacologically ablates endogenous microglia; optionally stopping administration of the CSF1R inhibitor for a time sufficient to prevent ablation of the transplanted donor microglia; and transplanting the donor microglia into the brain of the subject to provide the transplanted donor microglia.

In another aspect, a method of replacing endogenous microglia of a subject's brain, e.g., an adult subject, with transplanted donor microglia comprises genetically depleting at least a portion of the endogenous microglia by knocking out a Colony Stimulating Factor 1 Receptor (Csflr) gene, or overexpressing a toxin in the endogenous microglia; and transplanting the donor microglia into the brain of the subject to provide the transplanted donor microglia.

In yet another aspect, a method of preparing ablation-resistant donor microglia comprises engineering donor microglia to express a variant Colony Stimulating Factor 1 Receptor (variant CSF1R) that is resistant to a CSF1R inhibitor and providing ablation-resistant donor microglia.

BRIEF DESCRIPTION OF THE DRAWINGS

FIG. 2A shows the workflow for immunopanning. Dissociated cells are placed on a negative selection plate coated with a secondary antibody for non-specific cell binding and then a positive plate with CX3CR1 antibody for microglia. FIG. 2B shows representative images of isolated human microglia with typical flattened morphology (phase) and expression of IBA1 in >95% cells. FIG. 2C shows human microglia culture 5 days post purification is devoid of contamination with other brain cells such as GFAP+ astrocytes, TUJ1+ neurons, or OLIG2+ oligodendrocytes.

Figure 1A:
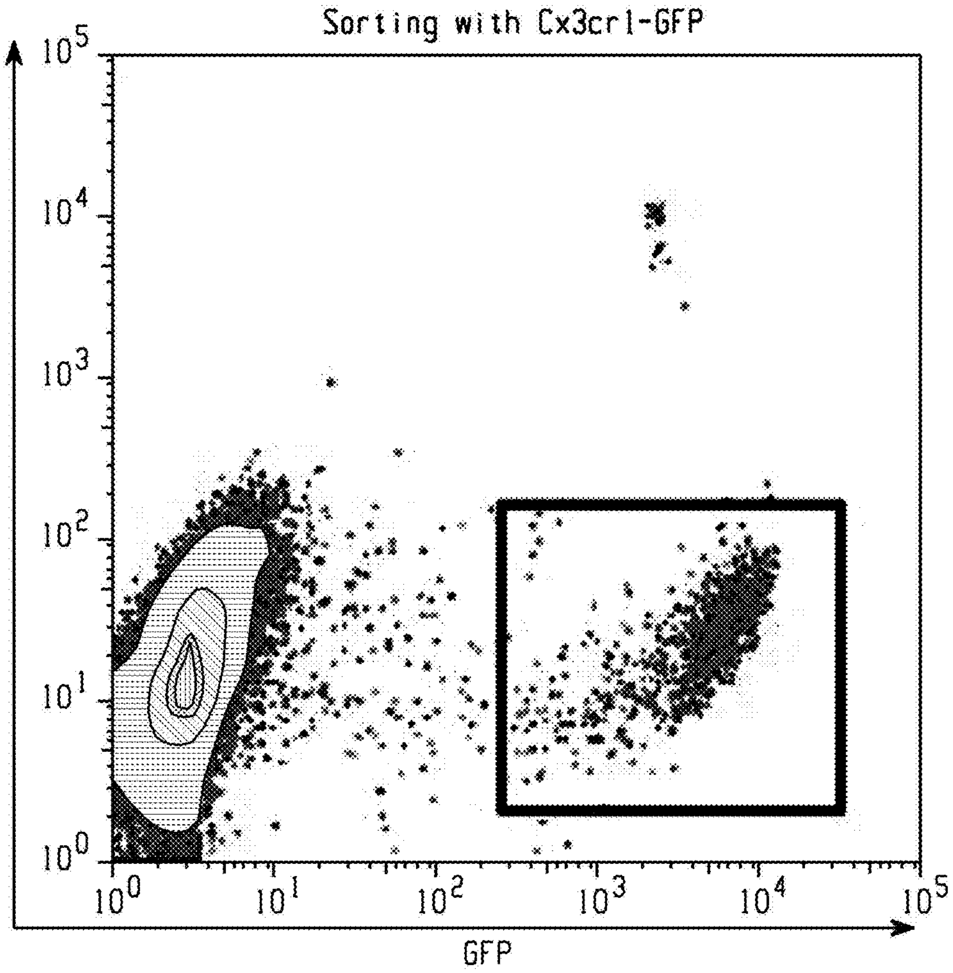
FIG. 1 shows FACS-based isolation of mouse microglia results in a pure microglia population based on GFP expression driven by the Cx3cr1 promoter and co-labeling with Iba1, a microglia-specific marker.

The above-described and other features will be appreciated and understood by those skilled in the art from the following detailed description, drawings, and appended claims.

DETAILED DESCRIPTION

In an aspect, described herein are compositions and methods for the transplantation of microglia to the brain, particularly the adult brain, including the use of microglia as a vehicle for delivering therapeutic biologic agents or cells into the brain. The brain as a target for therapeutic agents has presented special challenges, such as the impenetrability of the blood-brain-barrier and the large surface area of the neocortex, which makes direct delivery of therapeutics by arrayed intracranial injections unfeasible. This has restricted the use of therapeutic biologic agents and cells for the treatment of a wide range of diseases, including neuropsychiatric disorders and neurodegenerative disorders such as Alzheimer's disease and related dementias.

The inventors have taken advantage of the ability of microglia to repopulate the brain, specifically the adult brain, with new cells by devising a method whereby transplanted microglia outcompete residual microglia for effective repopulation of the brain. Thus, described herein are compositions and methods for replacing endogenous microglia throughout large areas of the brain with transplanted microglia. The dispersed, transplanted microglia can be used to continuously deliver therapeutic biologic agents that would not otherwise cross the blood-brain barrier or that have short half-lives in serum, to replace defective microglia such as those implicated in causing neurodegenerative disorders such as Alzheimer's disease, to become another cell type, such as neurons via reprogramming, or other applications.

In an aspect, a method of replacing endogenous microglia of a subject's brain with transplanted donor microglia comprises depleting at least a portion of the endogenous microglia by administering to the subject a Colony Stimulating Factor 1 Receptor (CSF1R) inhibitor, wherein the CSF1R inhibitor is blood-brain barrier permeable and pharmacologically ablates endogenous microglia; optionally stopping administration of the CSF1R inhibitor for a time sufficient to prevent ablation of the transplanted donor microglia; and transplanting the donor microglia into the brain of the subject to provide the transplanted donor microglia. In an aspect, the subject is an adult subject.

Exemplary subjects include mammals and non-mammals, specifically mammals such as humans, mice, and pre-clinical large animals. Exemplary non-mammals include zebrafish and other vertebrates.

Exemplary donor microglia include donor microglia originating from a biopsy from the subject or a biopsy donor, or the donor microglia can originate from cultured stem cells, such as induced pluripotent stem cells or embryonic stem cells.

Donor microglia can be prepared by fluorescence-activated cell sorting (FACS) or immunopanning of heterogeneous brain cell suspensions such as from brain biopsies.

In a FACS protocol, heterogeneous brain cell suspensions are separated into sub-populations of cells using fluorescent labeling. A CX3CR1 antibody can be used for specific separation of microglia. In an aspect, microglia from a mouse brain can also be FACS sorted with the use of a GFP transgene expressed specifically in microglia.

In an immunopanning protocol, antibodies specific for the cell type of interest are absorbed onto a plate and heterogeneous brain cell suspensions are incubated on the plate allowing for selection of the cell type of interest, specifically microglia, from the heterogeneous brain cell suspension. A CX3CR1 antibody can be used for specific binding of microglia.

Alternatively, the donor microglia can originate from cultured stem cells, such as induced pluripotent stem cells (iPSCs) or embryonic stem cells. Methods to differentiate microglia from iPSCs or embryonic stem cells are known in the art. For example, microglia can be differentiated from iPSCs using a modification of macrophage differentiation protocols. In an aspect, microglia can be differentiated from iPSCs by first differentiating iPSCs to a mesodermal, hematopoietic lineage, then transferring non-adherent CD43+ hematopoietic progenitors to a media containing M-CSF, IL-34, and TGFβ-1 cytokines that promote differentiation of homeostatic microglia.

In order for the transplanted donor microglia to disperse through the neural parenchyma and repopulate the brain with new cells, the endogenous microglia of the subject must first be depleted. Depletion of endogenous microglia can be achieved pharmacologically and/or genetically. Pharmacological ablation can be done using a Colony Stimulating Factor 1 Receptor (CSF1R) inhibitor, specifically a blood-brain barrier permeable CSF1R inhibitor.

Exemplary CSF1R inhibitors include ABT-869, MCS110, PLX-3397, PLX-7486, JNJ-40346527, JNJ-28312141, ARRY-382, PLX-73086 (AC-708), DCC-3014, AZD6495, GW2580, Ki20227, BLZ945, PLX-647, PLX5622, imatinib, emactuzumab (RG7155; R05509554), Cabiralizumab (FPA-008), LY-3022855 (IMC-CS4), AMG-820, TG-3003, H27K15, 12-2D6, 2-4A5, GSK3196165, and LNA-anti-miR-155.

PLX5622 (6-fluoro-N-[(5-fluoro-2-methoxypyridin-3-yl)methyl]-5-[(5-methyl-1H-pyrrolo[2,3-b]pyridin-3-yl)methyl]pyridin-2-amine) has the formula:

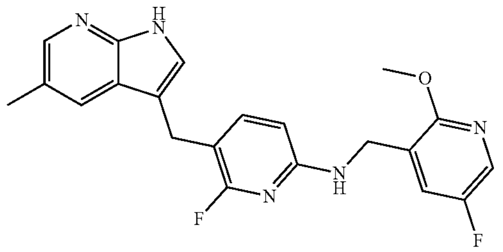 [SMILES: COc1ncc(F)cc1CNc1ccc(Cc2c[nH]c3ncc(C)cc23)c(F)n1]

Once the administered CSF1R inhibitor pharmacologically ablates endogenous microglia, the method can include stopping administration of the CSF1R inhibitor for a time sufficient to prevent ablation of transplanted donor microglia. Exemplary times include 1-3 days prior to transplantation.

Alternatively or preferably in addition to stopping administration of the CSF1R inhibitor for a time sufficient to prevent ablation of transplanted donor microglia, the transplanted donor microglia can be resistant to ablation by the CSF1R inhibitor. In an aspect, the transplanted donor microglia express a constitutively active variant CSF1R that is resistant to the CSF1R inhibitor. This method is particularly useful in treating human subjects, particularly adult human subjects.

In an aspect, a method of preparing ablation-resistant donor microglia comprises engineering donor microglia to express a constitutively active variant Colony Stimulating Factor 1 Receptor (variant CSF1R) that is resistant to a CSF1R inhibitor and providing the ablation-resistant donor microglia.

For example, based on the mechanism of action of PLX5622 which antagonizes the CSF1R receptor, variant forms of CSF1R that are constitutively active and should convey resistance to PLX5622 were screened. The $CSF1R^{L301S}$, $CSF1R^{Y571D}$ $CSF1R^{Y969F}$, $CSF1R^{delta706\text{-}712}$ mutants and combinations thereof identified in the screen exhibited high resistance to PLX5622-mediated microglial ablation. These or other variants of CSF1R can be expressed in donor microglia such as donor human microglia using retrovirus infection. The modified microglia that are resistant to the CSF1R inhibitor can then be transplanted into hosts in which the endogenous microglia are being continuously depleted pharmacologically with the CSF1R inhibitor post-translation to allow the donor microglia to outcompete the residual endogenous microglia.

Exemplary methods to express a constitutively active variant CSF1R in donor microglia include infection using viral vectors expressing the variant CSF1R such as adeno-associated virus, adenovirus, retrovirus, orthomyxovirus, paramyxovirus, papovavirus, picornavirus, lentivirus, herpes simplex virus, vaccinia virus, pox virus, or alphavirus vector. Methods of transducing cells such as microglia with viral vectors are well-known in the art. A transduction protocol typically includes engineering a recombinant virus carrying a transgene for the variant CSF1R, amplification of recombinant viral particles in a packaging cell line, purification and titration of amplified viral particles, and subsequent infection of the cells of interest with the virus particles carrying the transgene for the variant CSF1R.

Other methods such as CRISPR/Cas9 gene editing can also be used to introduce variant CSF1R into donor microglia. CRISPR refers to the Clustered Regularly Interspaced Short Palindromic Repeats type II system which enables bacteria and archaea to detect and silence foreign nucleic acids, e.g., from viruses or plasmids, in a sequence-specific manner. In type II systems, guide RNA interacts with Cas9 and directs the nuclease activity of Cas9 to target DNA sequences complementary to those present in the guide RNA. Guide RNA base pairs with complementary sequences in target DNA. Cas9 nuclease activity then generates a double-stranded break in the target DNA. CRISPR/Cas9 gene editing can be used to inactive genes or to insert genes into the genome of a cell.

Alternatively, in non-human subjects, the endogenous microglia of the can be genetically ablated by specifically knocking out Csflr or by overexpressing a toxin in the endogenous microglia. Genetic ablation in mice can be done using the following alleles: $Cx3cr1^{CreER/+}$, $Csflr^{fx/fx}$, $Rosa26^{iDTA/iDTA}$, which leads to the expression of diphtheria toxin and deletion of Csflr exclusively in microglia upon intraperitoneal tamoxifen administration. With daily injection of tamoxifen, donor microglia outcompete endogenous microglia for repopulation. Methods of knocking out a gene of interest include homologous recombination and CRISPR/Cas9. Methods of toxin overexpression include use for viral vectors and CRISPR/Cas9.

In an aspect a method of replacing endogenous microglia of a non-human subject's brain with transplanted donor microglia comprises genetically depleting at least a portion of the endogenous microglia by knocking out a Colony Stimulating Factor 1 Receptor (Csflr) gene, or overexpressing a toxin in the endogenous microglia; and transplanting the donor microglia into the brain of the non-human subject to provide the transplanted donor microglia. In an aspect the subject is an adult subject.

Exemplary subjects for the foregoing methods include subjects having a neurodevelopmental disorder, a psychiatric disorder, a neurodegenerative disorder, or neuronal damage related to stroke, traumatic brain injury or spinal cord injury. Neurodevelopmental disorders include intellectual disability (ID), learning disorders such as dyslexia and dyscalculia, autism spectrum disorders, motor disorders, tic disorders, traumatic brain injury, genetic neurodevelopmental disorders such as Down syndrome, disorders due to neurotoxicants such as fetal alcohol disorder, and attention deficit hyperactivity disorder. Psychiatric disorders include depression, bipolar disorder, schizophrenia, anxiety disorders, eating disorders and addictive behaviors. Neurodegenerative disorders include Alzheimer's disease, Parkinson's disease, Amyotrophic lateral sclerosis, Huntington's disease, Lewy body disease and spinal muscular atrophy.

One advantage of the donor microglia described herein is that they can be engineered to express a therapeutic biologic agent such as a protein, a peptide, a monoclonal antibody, or a therapeutic nucleic acid. Therapeutic proteins and peptides include the glycoprotein cytokine erythropoietin and other growth factors. Exemplary monoclonal antibodies include FAB fragments, single-chain variable fragments (scFV), single-domain antibodies (sdAB), humanized monoclonal antibodies and chimeric monoclonal antibodies. Exemplary therapeutic nucleic acids include antisense oligonucleotides, micro RNAs, short interfering RNAs, ribozymes, RNA decoys, circular RNAs, and aptamers. RNA therapeutics can act at the pre-mRNA level (by splicing modulation/correction using antisense oligonucleotides), at the mRNA level (inhibiting gene expression by siRNAs and antisense oligonucleotides), at the DNA level (by editing mutated sequences through the use of CRISPR/Cas9), or at the protein level by acting as agonists or antagonists.

In an aspect, the donor microglia express a therapeutic biologic agent, such as a therapeutic biologic agent that does not cross the blood brain barrier, and/or a biologic with a short half-life in circulation. Exemplary therapeutic biologic agents include proteins, peptides, monoclonal antibodies and nucleic acid therapeutics such as antisense oligonucleotides.

Exemplary therapeutic biologic agents used to treat stroke, traumatic brain injury or spinal cord injury include growth factors such as brain-derived neurotrophic factor (BDNF), epidermal growth factor plus erythropoietin, and human chorionic gonadotropin (hCG) plus erythropoietin. Antibodies that antagonize myelin-associated glycoprotein [MAG], oligo-myelin glycoprotein, and Nogo-A have been suggested as treatment for stroke. Anti High mobility group box 1 (HMGB1) protein antibodies have been suggested to prevent cognitive dysfunction after traumatic brain injury. Elezanumab (ABT-555) is a monoclonal antibody RGMa inhibitor being investigated to treat spinal cord injuries and acute ischemic stroke.

Psychiatric disorders such as depression, bipolar disorder, schizophrenia, anxiety disorders, eating disorders and addictive behaviors can be associated with elevated levels of pro-inflammatory cytokines interleukin IL-1, IL-6, tumor necrosis factor (TNF)-α, and C-reactive protein (CRP) compared to normal individuals. Monoclonal antibodies targeting pro-inflammatory cytokines include infliximab (Remicade®), adalimumab (Humira®), certolizumab pegol (Cimzia®), and golimumab (Simponi®).

Exemplary monoclonal antibodies for the treatment of Alzheimer's disease include the antimyeloid antibodies including aducanumab, crenezumab, gantenerumab, and solanezumab, and the anti-tau antibodies including LY3002813, ABBV-8E12, BIIB092, LY3303560, and RO7105705.

Exemplary monoclonal antibodies for the treatment of Parkinson's disease include BIIB054 and prasinezumab (PRX002/RG7935).

Exemplary monoclonal antibodies for the treatment of Amyotrophic lateral sclerosis include IC14, Ultomiris®, and ozanezumab, a humanised IgG monoclonal antibody against Nogo-A. Tofersen (BIIB067) is an antisense oligonucleotide that targets the genetic driver of ALS.

Exemplary monoclonal antibodies for the treatment of Huntington's disease include NCT02481674, bapineuzumab, and anti-semaphorin-4D (SEMA4D) antibodies.

Exemplary monoclonal antibodies for the treatment of Lewy body disease include PRX002/RG7935 (PRX002).

Exemplary monoclonal antibodies for the treatment of spinal muscular atrophy include a human anti-promyostatin monoclonal antibody SRK-015. Zolgensma® (onasemnogene abeparvovec-xioi) is an AveXis gene therapy treatment for spinal muscular atrophy (SMA). SPINRAZA® (nusinersen) is an antisense oligonucleotide that modulates alternative splicing of the SMN2 gene.

In another aspect, the donor microglia can comprise gene-corrected microglia to replace the endogenous microglia, potentially reversing disease progression. Recent studies on large-scale Alzheimer's risk genes show that many of the gene variants are expressed most highly in microglia. Exemplary Alzheimer's disease risk genes include apolipoprotein E (APOE), Amyloid precursor protein (APP), Presenilin 1 (PSEN1), and Presenilin 2 (PSEN2). Exemplary Parkinson's disease risk genes include SNCA (encoding α-synuclein), LRRK2 (encoding Leucine-rich repeat kinase 2), GBA, encoding the enzyme glucocerebrosidase, and MAPT (encoding microtubule-associated protein tau). Exemplary Amyotrophic lateral sclerosis risk genes include SOD1 (encoding superoxide dismutase 1), TARDBP (encoding TAR DNA binding protein) and FUS (encoding FUS RNA binding protein). Exemplary Huntington's disease risk genes include HTT (encoding the huntingtin protein). Exemplary spinal muscular atrophy risk genes include SMA1 (encoding the motor neuron protein SMN).

In another aspect, when the subject has a neurodegenerative disease, or neuronal damage related to stroke, traumatic brain injury or spinal cord injury, for example, the transplanted donor microglia are converted to neurons after transplantation. Donor microglia can be used as a vehicle for introducing widely dispersed new neurons in neurodegenerative diseases. A hallmark of neurodegenerative diseases such as Alzheimer's disease, stroke, and spinal cord injury, for example, is the damage to neurons. Replacement of the damaged neurons is an attractive therapeutic direction. Previous studies have shown that neuro-precursor cell grafts generate neurons that functionally integrate into the adult mouse brain. However, a dispersion technique such as the microglial transplantation technique described herein is needed to avoid having to do densely arrayed cell injections, which would result in considerable damage. This is particularly relevant for conditions that afflict the neocortex (with an area of 0.2 to 0.25 $m^2$ folded into convoluted sulci and gyri). It has been shown that microglia can be converted to neurons. Thus, the methods described herein can be used to introduce widely dispersed microglia that can then be induced to become new neurons.

Microglia can be induced to become neurons by using defined transcription factors (TFs) and/or microRNAs. Examples of transcription factors that are used to reprogram microglia to neurons include BRN2, ASCL1, MYT1L, NGN2, and NEUROD1. Examples of miRNAs used to reprogram to a neuronal fate include miRNA-9/9* and miRNA-124.

The methods described herein will significantly advance the treatment of neurodevelopmental, neurodegenerative, and psychiatric disorders in addition to stroke, traumatic brain injury and spinal cord injury by allowing the delivery of microglia and therapeutic biologic agents to the brain, while minimizing invasive transplantations that require multiple injections.

The invention is further illustrated by the following non-limiting examples.

EXAMPLES

Example 1: Source of Donor Microglia

For a proof-of-principle, primary microglia were used. The protocol involves the reliable isolation of both highly pure mouse and human primary microglia.

Figure 1B:
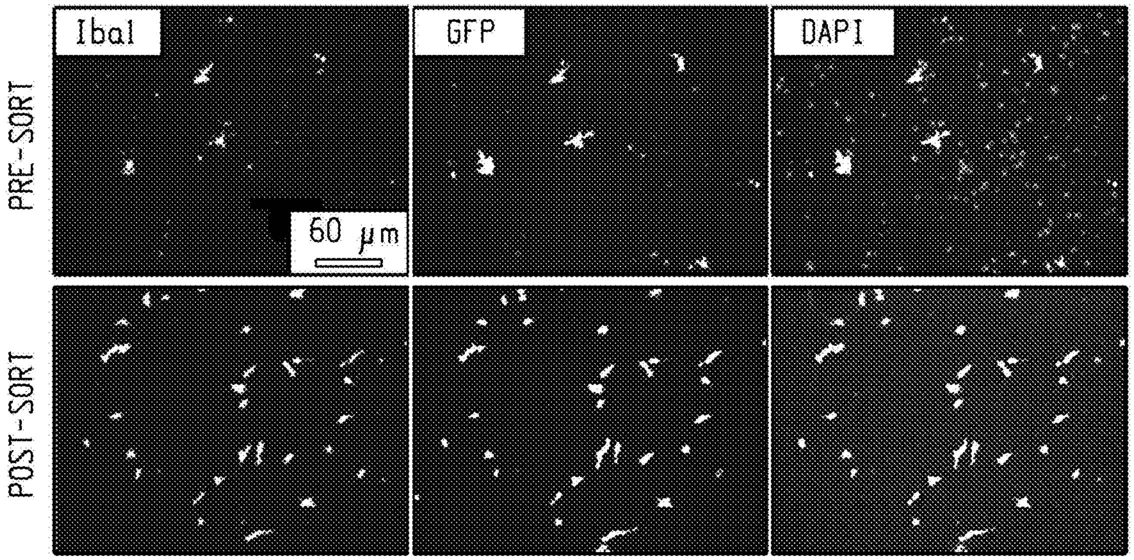

For mouse, purification by FACS of GFP-expressing microglia from a $Cx3cr1^{GFP}$ mouse line yields approximately 100% microglia, confirmed by co-labeling for GFP and a microglia marker, IBA1 (FIG. 1).

Figure 2A:
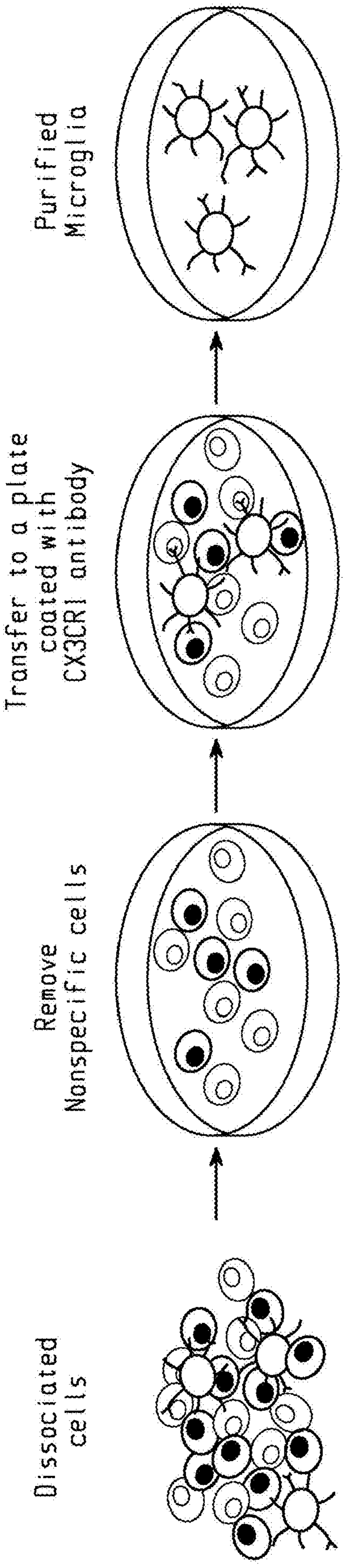
FIGS. 2A-C show the workflow and results for immunopanning microglia.
Figure 2B:
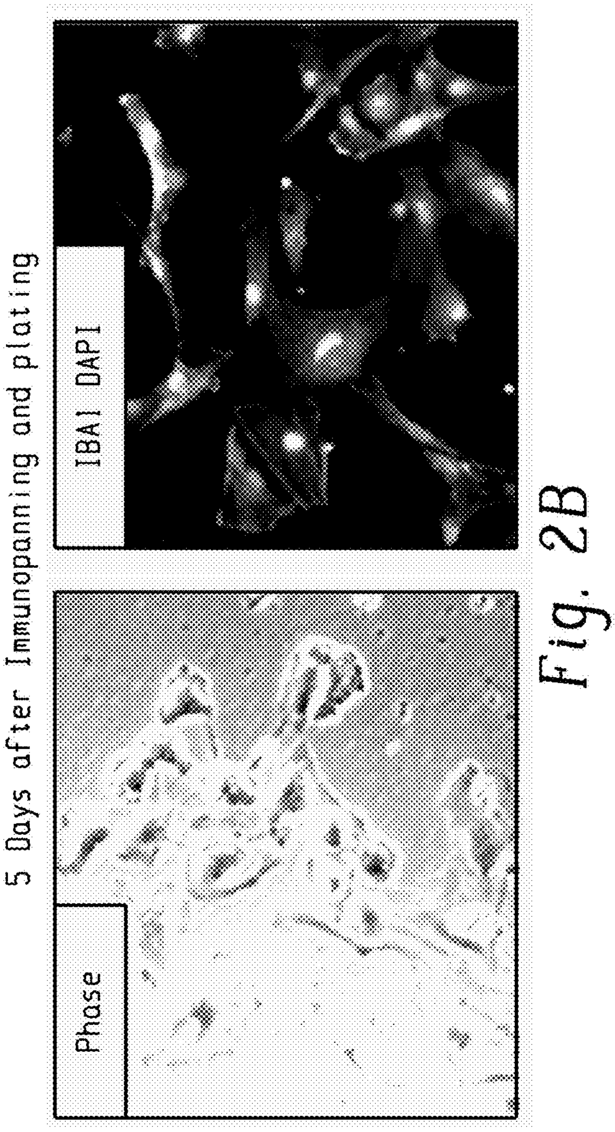
Figure 2C:
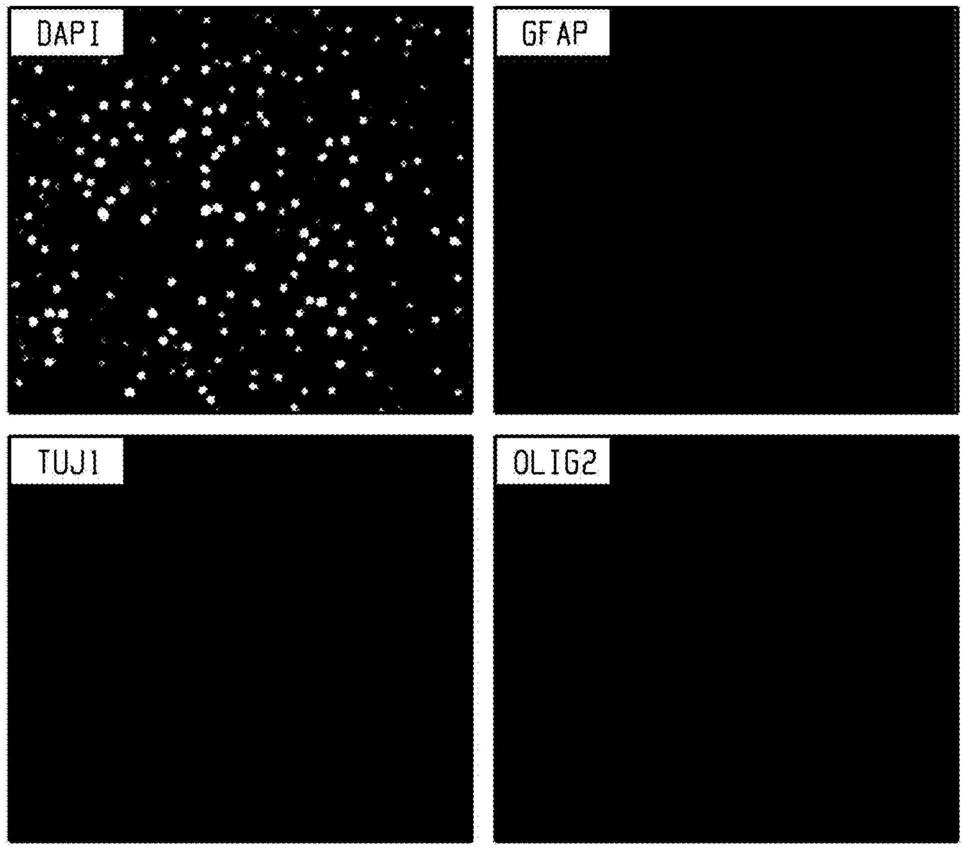

For primary human microglia, purification by immunopanning (FIG. 2A), a process that imposes minimal physical stress, yields an initially >95% pure human microglia population. The process involves placing dissociated brain cells on a negative selection plate coated with a secondary antibody for non-specific cell binding and then a positive plate with CX3CR1 antibody for specific binding of microglia. After several washes of the plate, bound microglia are detached from the plate with an enzyme trypsin and collected by centrifugation. The isolated microglia are viable and proliferative, and after 5 days in microglia media remain the only detectable cell type in culture (FIG. 2B-C).

Example 2: Preparation of Subject for Transplantation

Microglia in the host subject must be depleted before transplantation of donor microglia, otherwise the transplanted microglia will not disperse throughout the neural parenchyma and will not repopulate the brain with new cells. Depletion of host microglia can be accomplished pharmacologically using a Colony Stimulating Factor 1 receptor (CSF1R) inhibitor, or genetically by specifically knocking out Csflr or overexpressing a toxin specifically in the host microglia. For proof-of-concept in mice, host microglia were ablated pharmacologically before transplantation, and host microglia were genetically ablated after transplantation to allow the transplanted microglia to outcompete residual host microglia. In an aspect, the need for a genetic ablation (which may not be clinically relevant) can be obfuscated using donor microglia that are rendered resistant to the CSF1R inhibitor (see below). It is believed that transient depletion of microglia in a host does not appear to have negative side-effects on brain function.

Figure 3:
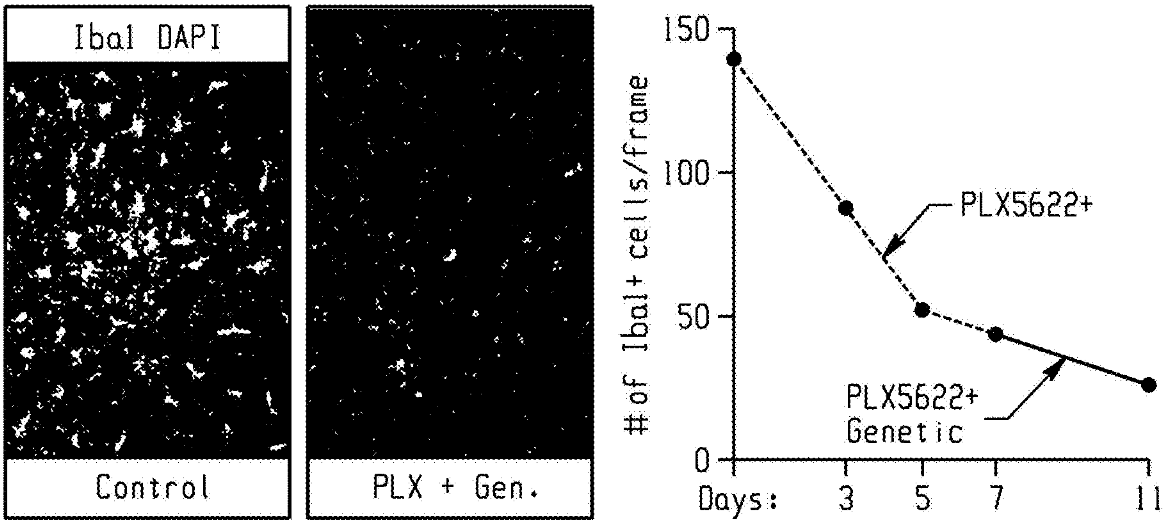
FIG. 3 left panel shows the extent of microglia ablation in vivo shown by Iba1 staining before and after pharmacological ablation with PLX5622 for 21 days with and without subsequent genetic ablation for 4 days. The right panel shows the quantitation. n>3/time point.

For pharmacological ablation of host microglia, PLX5622 (Plexxikon Inc.), a drug that inhibits CSF1R, was given to the mice via chow for 7 days prior to transplantation. This treatment kills approximately 90% of host microglia (FIG. 3). PLX5622 is a blood-brain-barrier permeable drug in clinical trials. Two days before transplantation, PLX5622 treatment was stopped to avoid potentially killing donor cells. On the same day, genetic ablation of endogenous microglia was initiated in host mice using the following alleles: $Cx3cr1^{CreER/+}$; $Csf1^{rfx/fx}$; $Rosa26^{iDTA/DTA}$, which leads to expression of diphtheria toxin and deletion of Csflr exclusively in microglia upon intraperitoneal tamoxifen administration. Thus, with daily injection of tamoxifen, donor microglia outcompete host microglia for repopulation.

Figure 4:
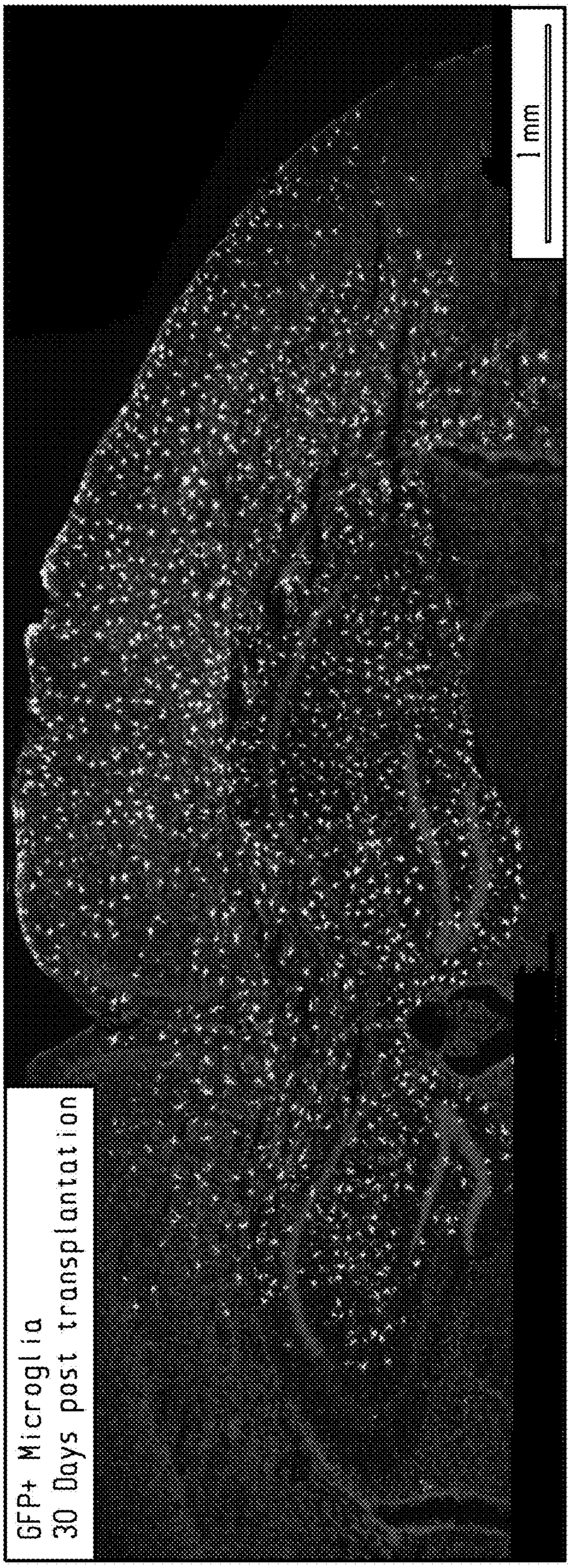
FIG. 4 shows a single injection of approximately 2000 GFP+ mouse microglia leads to repopulation of the cortex after 30 days over an area spanning 8 mm in width.

Transplantation of mouse donor microglia into host subjects in which endogenous microglia had been depleted pharmacologically with PLX5622 and genetically with tamoxifen treatment, results in dispersion in the parenchyma up to at least 8 mm from the transplant site by 30 days (FIG. 4). It is believed that his is much farther dispersion than observed in any previous cell transplantation. These data confirm the importance of eliminating competition between host and donor microglia so that donor microglia can outcompete and disperse throughout the brain parenchyma.

Figure 5:
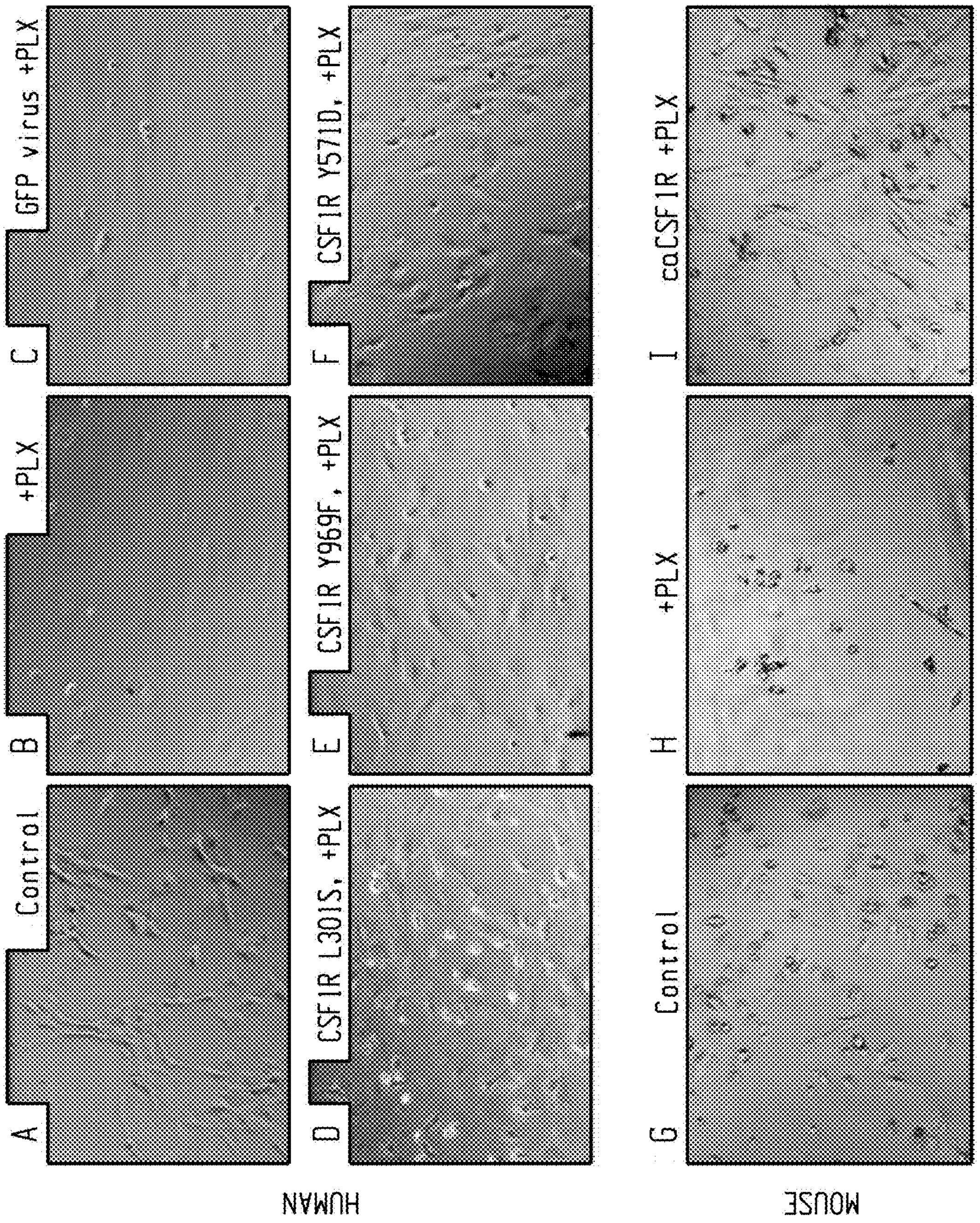
FIGS. 5A-I show screening of human and mouse microglia for resistance to PLX5622. Human microglia (5A) are normally susceptible to CSF1R antagonist PLX5622-induced cell death (5B). Screening of gain of function CSF1R mutants (5D-F) in human microglia showed resistance to PLX5622 when L301S mutant (5D) was overexpressed, followed by Y969F (5E) and Y571D 5(F). Similarly, mouse microglia (5G) are normally susceptible to CSF1R antagonist-induced cell death (5H). Screening of gain-of-function CSF1R mutants in mouse microglia also showed resistance to PLX5622 killing, an example of which is shown (5I).

There are at least two routes that can be used to deliver microglia into the brain. A direct intracranial injection can be used, as we did in this initial proof-of-concept (FIG. 5).

Alternatively, a less invasive intranasal deposition can be used. Using either method, the microglia can then expand and repopulate the brain.

Example 3: Donor Microglia Resistant to the CSF1R Inhibitor

Although dispersion of mouse microglia was achieved using the protocol described in Example 2, continued genetic ablation of host microglia after transplantation of donor microglia cannot likely be used in a clinical setting. Therefore, to achieve dispersion of microglia independent of any genetic manipulations, a novel method to make microglia resistant to ablation by a CSF1R inhibitor such as PLX5622 was developed. Based on the mechanism of action of PLX5622 (antagonizing the critical CSF1R receptor), mutant forms of CSF1R that are constitutively active and potentially convey resistance to PLX5622 were screened (FIG. 5). Of the mutant CSF1R forms tested, several ($CSF1R^{L301S}$, $CSF1R^{Y571D}$, $CSF1R^{Y969F}$, $CSF1R^{delta706-712}$) exhibited high resistance to PLX5622-mediated cell ablation when expressed in cultured human primary microglia. Mutant CSF1Rs were expressed in human donor microglia via retrovirus infection. Such PLX5622-resistant microglia can then be transplanted to hosts in which endogenous microglia are continuously being depleted pharmacologically with PLX5622 post transplantation to allow donor microglia to outcompete residual endogenous microglia for repopulation. We are currently testing resistance of microglia expressing $CSF1R^{L301S}$ and others to PLX5622 ablation in vivo.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of preparing ablation-resistant donor microglia, comprising engineering donor microglia to express a constitutively active variant Colony Stimulating Factor 1 Receptor (variant CSF1R) that is resistant to a CSF1R inhibitor and providing ablation-resistant donor microglia, wherein the CSF1R inhibitor is PLX5622 and wherein the constitutively active variant CSF1R is selected from the group consisting of $CSF1R^{L301S}$, $CSF1R^{Y571D}$, $CSF1R^{Y969F}$, or $CSF1R^{delta706-712}$.

2. The method of claim 1, wherein engineering the donor microglia comprises expressing the CSF1R that is resistant to the CSF1R inhibitor using viral infection or CRISPR/Cas9 gene editing.

* * * * *